US012629201B2

(12) United States Patent
Govari et al.

(10) Patent No.:   US 12,629,201 B2
(45) Date of Patent:       May 19, 2026

(54) MULTI-FORM CATHETER

(71) Applicant: Biosense Webster (Israel) Ltd.,
Yokneam (IL)

(72) Inventors: Assaf Govari, Haifa (IL); **Christopher
Thomas Beeckler**, Brea, CA (US);
Joseph Thomas Keyes, Sierra Madre,
CA (US); Justin George Lichter,
Irvine, CA (US)

(73) Assignee: Biosense Webster (Israel) Ltd.,
Yokneam (IL)

( * ) Notice: Subject to any disclaimer, the term of this
patent is extended or adjusted under 35
U.S.C. 154(b) by 756 days.

(21) Appl. No.: 17/566,415

(22) Filed: Dec. 30, 2021

(65) Prior Publication Data

US 2023/0210590 A1      Jul. 6, 2023

(51) Int. Cl.
*A61B 18/14*         (2006.01)
*A61B 17/00*         (2006.01)
(Continued)

(52) U.S. Cl.
CPC   *A61B 18/1492* (2013.01); *A61B 2017/00867*
(2013.01); *A61B 2018/00267* (2013.01);
(Continued)

(58) Field of Classification Search
CPC ...... A61B 18/1492; A61B 2017/00867; A61B
2018/0016; A61B 2018/00196; A61B
2018/00267; A61B 2018/00351; A61B
2018/00357; A61B 2018/00375; A61B
2018/00577; A61B 2018/00839; A61B
5/287; A61B 5/367; A61M 25/0074
See application file for complete search history.

(56) References Cited

U.S. PATENT DOCUMENTS 4,699,147 A     10/1987   Chilson et al.
4,940,064 A      7/1990   Desai
(Continued)

FOREIGN PATENT DOCUMENTS

CN         111248993 A      6/2020
CN         111248996 A      6/2020
(Continued)

OTHER PUBLICATIONS

Extended European Search Report dated May 24, 2023, from
corresponding European Application No. 22217125.8.

*Primary Examiner* — Tigist S Demie

(57)              ABSTRACT

In one exemplary mode, a catheter apparatus includes an
elongated deflectable element including a distal end, a
flexible puller including a distal portion, and configured to
be retracted through the deflectable element, and an expand-
able assembly including a plurality of resilient splines, each
resilient spline including at least one electrode disposed
thereon, the resilient splines being disposed circumferen-
tially around the distal portion of the puller, with first ends
of the splines being coupled with the distal end of the
deflectable element and second ends of the splines coupled
with the distal portion of the puller, the splines being
configured to bow radially outward in a relaxed form of the
expandable assembly and bow further radially outward
when the puller is retracted expanding the expandable
assembly from the relaxed form to an expanded form.

17 Claims, 5 Drawing Sheets

(51) Int. Cl.
   *A61B 18/00* (2006.01)
   *A61M 25/00* (2006.01)
(52) U.S. Cl.
   CPC .............. *A61B 2018/00351* (2013.01); *A61B 2018/00577* (2013.01); *A61M 25/0074* (2013.01)

(56) References Cited

U.S. PATENT DOCUMENTS

| | | | |
|---|---|---|---|
| 5,215,103 A | 6/1993 | Desai |
| 5,255,679 A | 10/1993 | Imran |
| 5,293,869 A | 3/1994 | Edwards et al. |
| 5,309,910 A | 5/1994 | Edwards et al. |
| 5,313,943 A | 5/1994 | Houser et al. |
| 5,324,284 A | 6/1994 | Imran |
| 5,345,936 A | 9/1994 | Pomeranz et al. |
| 5,365,926 A | 11/1994 | Desai |
| 5,396,887 A | 3/1995 | Imran |
| 5,400,783 A | 3/1995 | Pomeranz et al. |
| 5,411,025 A | 5/1995 | Webster, Jr. |
| 5,415,166 A | 5/1995 | Imran |
| 5,456,254 A | 10/1995 | Pietroski et al. |
| 5,465,717 A | 11/1995 | Imran et al. |
| 5,476,495 A | 12/1995 | Kordis et al. |
| 5,499,981 A | 3/1996 | Kordis |
| 5,526,810 A | 6/1996 | Wang |
| 5,546,940 A | 8/1996 | Panescu et al. |
| 5,549,108 A | 8/1996 | Edwards et al. |
| 5,558,073 A | 9/1996 | Pomeranz et al. |
| 5,577,509 A | 11/1996 | Panescu et al. |
| 5,595,183 A | 1/1997 | Swanson et al. |
| 5,598,848 A | 2/1997 | Swanson et al. |
| 5,609,157 A | 3/1997 | Panescu et al. |
| 5,628,313 A | 5/1997 | Webster, Jr. |
| 5,681,280 A | 10/1997 | Rusk et al. |
| 5,722,401 A | 3/1998 | Pietroski et al. |
| 5,722,403 A | 3/1998 | McGee et al. |
| 5,725,525 A | 3/1998 | Kordis |
| 5,730,128 A | 3/1998 | Pomeranz et al. |
| 5,772,590 A | 6/1998 | Webster, Jr. |
| 5,782,899 A | 7/1998 | Imran |
| 5,823,189 A | 10/1998 | Kordis |
| 5,881,727 A | 3/1999 | Edwards |
| 5,893,847 A | 4/1999 | Kordis |
| 5,904,680 A | 5/1999 | Kordis et al. |
| 5,911,739 A | 6/1999 | Kordis et al. |
| 5,928,228 A | 7/1999 | Kordis et al. |
| 5,968,040 A | 10/1999 | Swanson et al. |
| 6,014,579 A | 1/2000 | Pomeranz et al. |
| 6,014,590 A | 1/2000 | Whayne et al. |
| 6,119,030 A | 9/2000 | Morency |
| 6,216,043 B1 | 4/2001 | Swanson et al. |
| 6,216,044 B1 | 4/2001 | Kordis |
| 6,428,537 B1 | 8/2002 | Swanson et al. |
| 6,456,864 B1 | 9/2002 | Swanson et al. |
| 6,574,492 B1 | 6/2003 | Ben-Haim et al. |
| 6,584,345 B2 | 6/2003 | Govari |
| 6,600,948 B2 | 7/2003 | Ben-Haim et al. |
| 6,738,655 B1 | 5/2004 | Sen et al. |
| 6,741,878 B2 | 5/2004 | Fuimaono et al. |
| 6,748,255 B2 | 6/2004 | Fuimaono et al. |
| 6,780,183 B2 | 8/2004 | Jimenez, Jr. et al. |
| 6,837,886 B2 | 1/2005 | Collins et al. |
| 6,866,662 B2 | 3/2005 | Fuimaono et al. |
| 6,892,091 B1 | 5/2005 | Ben-Haim et al. |
| 6,970,730 B2 | 11/2005 | Fuimaono et al. |
| 6,973,340 B2 | 12/2005 | Fuimaono et al. |
| 6,980,858 B2 | 12/2005 | Fuimaono et al. |
| 7,048,734 B1 | 5/2006 | Fleischman et al. |
| 7,149,563 B2 | 12/2006 | Fuimaono et al. |
| 7,255,695 B2 | 8/2007 | Falwell et al. |
| 7,257,434 B2 | 8/2007 | Fuimaono et al. |
| 7,399,299 B2 | 7/2008 | Daniel et al. |
| 7,410,486 B2 | 8/2008 | Fuimaono et al. |
| 7,522,950 B2 | 4/2009 | Fuimaono et al. |
| RE41,334 E | 5/2010 | Beatty et al. |
| 7,846,157 B2 | 12/2010 | Kozel |
| 7,930,018 B2 | 4/2011 | Harlev et al. |
| 8,007,495 B2 | 8/2011 | McDaniel et al. |
| 8,048,063 B2 | 11/2011 | Aeby et al. |
| 8,103,327 B2 | 1/2012 | Harlev et al. |
| 8,167,845 B2 | 5/2012 | Wang et al. |
| 8,224,416 B2 | 7/2012 | De La Rama et al. |
| 8,235,988 B2 | 8/2012 | Davis et al. |
| 8,346,339 B2 | 1/2013 | Kordis et al. |
| 8,435,232 B2 | 5/2013 | Aeby et al. |
| 8,447,377 B2 | 5/2013 | Harlev et al. |
| 8,498,686 B2 | 7/2013 | Grunewald |
| 8,517,999 B2 | 8/2013 | Pappone et al. |
| 8,545,490 B2 | 10/2013 | Mihajlovic et al. |
| 8,560,086 B2 | 10/2013 | Just et al. |
| 8,567,265 B2 | 10/2013 | Aeby et al. |
| 8,712,550 B2 | 4/2014 | Grunewald |
| 8,755,861 B2 | 6/2014 | Harlev et al. |
| 8,825,130 B2 | 9/2014 | Just et al. |
| 8,906,011 B2 | 12/2014 | Gelbart et al. |
| 8,945,120 B2 | 2/2015 | McDaniel et al. |
| 8,979,839 B2 | 3/2015 | De La Rama et al. |
| 9,037,264 B2 | 5/2015 | Just et al. |
| 9,131,980 B2 | 9/2015 | Bloom |
| 9,204,929 B2 | 12/2015 | Solis |
| 9,277,960 B2 | 3/2016 | Weinkam et al. |
| 9,314,208 B1 | 4/2016 | Altmann et al. |
| 9,339,331 B2 | 5/2016 | Tegg et al. |
| 9,486,282 B2 | 11/2016 | Solis |
| 9,554,718 B2 | 1/2017 | Bar-Tal et al. |
| D782,686 S | 3/2017 | Werneth et al. |
| 9,585,588 B2 | 3/2017 | Marecki et al. |
| 9,597,036 B2 | 3/2017 | Aeby et al. |
| 9,687,297 B2 | 6/2017 | Just et al. |
| 9,693,733 B2 | 7/2017 | Altmann et al. |
| 9,782,099 B2 | 10/2017 | Williams et al. |
| 9,788,895 B2 | 10/2017 | Solis |
| 9,801,681 B2 | 10/2017 | Laske et al. |
| 9,814,618 B2 | 11/2017 | Nguyen et al. |
| 9,833,161 B2 | 12/2017 | Govari |
| 9,894,756 B2 | 2/2018 | Weinkam et al. |
| 9,895,073 B2 | 2/2018 | Solis |
| 9,907,609 B2 | 3/2018 | Cao et al. |
| 9,974,460 B2 | 5/2018 | Wu et al. |
| 9,986,949 B2 | 6/2018 | Govari et al. |
| 9,993,160 B2 | 6/2018 | Salvestro et al. |
| 10,014,607 B1 | 7/2018 | Govari et al. |
| 10,028,376 B2 | 7/2018 | Weinkam et al. |
| 10,034,637 B2 | 7/2018 | Harlev et al. |
| 10,039,494 B2 | 8/2018 | Altmann et al. |
| 10,045,707 B2 | 8/2018 | Govari |
| 10,078,713 B2 | 9/2018 | Auerbach et al. |
| 10,111,623 B2 | 10/2018 | Jung et al. |
| 10,130,420 B2 | 11/2018 | Basu et al. |
| 10,136,828 B2 | 11/2018 | Houben et al. |
| 10,143,394 B2 | 12/2018 | Solis |
| 10,172,536 B2 | 1/2019 | Maskara et al. |
| 10,182,762 B2 | 1/2019 | Just et al. |
| 10,194,818 B2 | 2/2019 | Williams et al. |
| 10,201,311 B2 | 2/2019 | Chou et al. |
| 10,219,860 B2 | 3/2019 | Harlev et al. |
| 10,219,861 B2 | 3/2019 | Just et al. |
| 10,231,328 B2 | 3/2019 | Weinkam et al. |
| 10,238,309 B2 | 3/2019 | Bar-Tal et al. |
| 10,278,590 B2 | 5/2019 | Salvestro et al. |
| D851,774 S | 6/2019 | Werneth et al. |
| 10,314,505 B2 | 6/2019 | Williams et al. |
| 10,314,507 B2 | 6/2019 | Govari et al. |
| 10,314,648 B2 | 6/2019 | Ge et al. |
| 10,314,649 B2 | 6/2019 | Bakos et al. |
| 10,349,855 B2 | 7/2019 | Zeidan et al. |
| 10,350,003 B2 | 7/2019 | Weinkam et al. |
| 10,362,991 B2 | 7/2019 | Tran et al. |
| 10,375,827 B2 | 8/2019 | Weinkam et al. |
| 10,376,170 B2 | 8/2019 | Quinn et al. |
| 10,376,221 B2 | 8/2019 | Iyun et al. |
| 10,398,348 B2 | 9/2019 | Osadchy et al. |
| 10,403,053 B2 | 9/2019 | Katz et al. |

(56) References Cited

U.S. PATENT DOCUMENTS

| | | | |
|---|---|---|---|
| 10,441,188 B2 | 10/2019 | Katz et al. | |
| 10,470,682 B2 | 11/2019 | Deno et al. | |
| 10,470,714 B2 | 11/2019 | Altmann et al. | |
| 10,482,198 B2 | 11/2019 | Auerbach et al. | |
| 10,492,857 B2 | 12/2019 | Guggenberger et al. | |
| 10,542,620 B2 | 1/2020 | Weinkam et al. | |
| 10,575,743 B2 | 3/2020 | Basu et al. | |
| 10,575,745 B2 | 3/2020 | Solis | |
| 10,582,871 B2 | 3/2020 | Williams et al. | |
| 10,582,894 B2 | 3/2020 | Ben Zrihem et al. | |
| 10,596,346 B2 | 3/2020 | Aeby et al. | |
| 10,602,947 B2 | 3/2020 | Govari et al. | |
| 10,617,867 B2 | 4/2020 | Viswanathan et al. | |
| 10,660,702 B2 | 5/2020 | Viswanathan et al. | |
| 10,667,753 B2 | 6/2020 | Werneth et al. | |
| 10,674,929 B2 | 6/2020 | Houben et al. | |
| 10,681,805 B2 | 6/2020 | Weinkam et al. | |
| 10,682,181 B2 | 6/2020 | Cohen et al. | |
| 10,687,892 B2 | 6/2020 | Long et al. | |
| 10,702,178 B2 | 7/2020 | Dahlen et al. | |
| 10,716,477 B2 | 7/2020 | Salvestro et al. | |
| 10,758,304 B2 | 9/2020 | Aujla | |
| 10,765,371 B2 | 9/2020 | Hayam et al. | |
| 10,772,566 B2 | 9/2020 | Aujila | |
| 10,799,281 B2 | 10/2020 | Goertzen et al. | |
| 10,842,558 B2 | 11/2020 | Harlev et al. | |
| 10,842,561 B2 | 11/2020 | Viswanathan et al. | |
| 10,863,914 B2 | 12/2020 | Govari et al. | |
| 10,881,376 B2 | 1/2021 | Shemesh et al. | |
| 10,898,139 B2 | 1/2021 | Guta et al. | |
| 10,905,329 B2 | 2/2021 | Bar-Tal et al. | |
| 10,912,484 B2 | 2/2021 | Ziv-Ari et al. | |
| 10,918,306 B2 | 2/2021 | Govari et al. | |
| 10,939,871 B2 | 3/2021 | Altmann et al. | |
| 10,952,795 B2 | 3/2021 | Cohen et al. | |
| 10,973,426 B2 | 4/2021 | Williams et al. | |
| 10,973,461 B2 | 4/2021 | Baram et al. | |
| 10,987,045 B2 | 4/2021 | Basu et al. | |
| 11,006,902 B1 | 5/2021 | Bonyak et al. | |
| 11,040,208 B1 | 6/2021 | Govari et al. | |
| 11,045,628 B2 | 6/2021 | Beeckler et al. | |
| 11,051,877 B2 | 7/2021 | Sliwa et al. | |
| 11,109,788 B2 | 9/2021 | Rottmann et al. | |
| 11,116,435 B2 | 9/2021 | Urman et al. | |
| 11,129,574 B2 | 9/2021 | Cohen et al. | |
| 11,160,482 B2 | 11/2021 | Solis | |
| 11,164,371 B2 | 11/2021 | Yellin et al. | |
| 2004/0210121 A1 | 10/2004 | Fuimaono et al. | |
| 2006/0009689 A1 | 1/2006 | Fuimaono et al. | |
| 2006/0009690 A1 | 1/2006 | Fuimaono et al. | |
| 2006/0100669 A1 | 5/2006 | Fuimaono et al. | |
| 2007/0083194 A1* | 4/2007 | Kunis | A61B 18/1492 |
| | | | 606/41 |
| 2007/0093806 A1 | 4/2007 | Desai et al. | |
| 2007/0276212 A1 | 11/2007 | Fuimaono et al. | |
| 2008/0097422 A1* | 4/2008 | Edwards | A61B 18/1492 |
| | | | 606/34 |
| 2008/0234564 A1 | 9/2008 | Beatty et al. | |
| 2011/0118726 A1 | 5/2011 | De La Rama et al. | |
| 2011/0160574 A1 | 6/2011 | Harlev et al. | |
| 2011/0190625 A1 | 8/2011 | Harlev et al. | |
| 2011/0245756 A1 | 10/2011 | Arora et al. | |
| 2011/0301597 A1 | 12/2011 | McDaniel et al. | |
| 2012/0271140 A1* | 10/2012 | Kordis | A61B 5/283 |
| | | | 600/375 |
| 2013/0172872 A1 | 7/2013 | Subramaniam et al. | |
| 2013/0172883 A1 | 7/2013 | Lopes et al. | |
| 2013/0178850 A1 | 7/2013 | Lopes et al. | |
| 2013/0190587 A1 | 7/2013 | Lopes et al. | |
| 2013/0296852 A1 | 11/2013 | Madjarov et al. | |
| 2014/0025069 A1 | 1/2014 | Willard et al. | |
| 2014/0052118 A1 | 2/2014 | Laske et al. | |
| 2014/0180147 A1 | 6/2014 | Thakur et al. | |
| 2014/0180151 A1 | 6/2014 | Maskara et al. | |
| 2014/0180152 A1 | 6/2014 | Maskara et al. | |
| 2014/0257069 A1 | 9/2014 | Eliason et al. | |
| 2014/0276712 A1 | 9/2014 | Mallin et al. | |
| 2014/0309512 A1 | 10/2014 | Govari et al. | |
| 2014/0350552 A1 | 11/2014 | Highsmith | |
| 2015/0011991 A1 | 1/2015 | Buysman et al. | |
| 2015/0045863 A1 | 2/2015 | Litscher et al. | |
| 2015/0080693 A1 | 3/2015 | Solis | |
| 2015/0105770 A1 | 4/2015 | Amit | |
| 2015/0119878 A1 | 4/2015 | Heisel et al. | |
| 2015/0133919 A1 | 5/2015 | McDaniel et al. | |
| 2015/0157402 A1 | 6/2015 | Kunis et al. | |
| 2015/0208942 A1 | 7/2015 | Bar-Tal et al. | |
| 2015/0223757 A1* | 8/2015 | Werneth | A61B 5/283 |
| | | | 600/301 |
| 2015/0250424 A1 | 9/2015 | Govari et al. | |
| 2015/0270634 A1 | 9/2015 | Buesseler et al. | |
| 2015/0342532 A1 | 12/2015 | Basu et al. | |
| 2016/0081746 A1 | 3/2016 | Solis | |
| 2016/0113582 A1 | 4/2016 | Altmann et al. | |
| 2016/0113709 A1 | 4/2016 | Maor | |
| 2016/0183877 A1 | 6/2016 | Williams et al. | |
| 2016/0228023 A1 | 8/2016 | Govari | |
| 2016/0228062 A1 | 8/2016 | Altmann et al. | |
| 2016/0278853 A1 | 9/2016 | Ogle et al. | |
| 2016/0302858 A1 | 10/2016 | Bencini | |
| 2016/0338770 A1 | 11/2016 | Bar-Tal et al. | |
| 2017/0027638 A1* | 2/2017 | Solis | A61B 18/1492 |
| 2017/0065227 A1 | 3/2017 | Marrs et al. | |
| 2017/0071543 A1 | 3/2017 | Basu et al. | |
| 2017/0071544 A1 | 3/2017 | Basu et al. | |
| 2017/0071665 A1 | 3/2017 | Solis | |
| 2017/0095173 A1 | 4/2017 | Bar-Tal et al. | |
| 2017/0100187 A1 | 4/2017 | Basu et al. | |
| 2017/0143227 A1 | 5/2017 | Marecki et al. | |
| 2017/0156790 A1 | 6/2017 | Aujla | |
| 2017/0172442 A1 | 6/2017 | Govari | |
| 2017/0185702 A1 | 6/2017 | Auerbach et al. | |
| 2017/0202515 A1 | 7/2017 | Zrihem et al. | |
| 2017/0221262 A1 | 8/2017 | Laughner et al. | |
| 2017/0224958 A1 | 8/2017 | Cummings et al. | |
| 2017/0265812 A1 | 9/2017 | Williams et al. | |
| 2017/0281031 A1 | 10/2017 | Houben et al. | |
| 2017/0281268 A1 | 10/2017 | Tran et al. | |
| 2017/0296125 A1 | 10/2017 | Altmann et al. | |
| 2017/0296251 A1 | 10/2017 | Wu et al. | |
| 2017/0347959 A1 | 12/2017 | Guta et al. | |
| 2017/0354338 A1 | 12/2017 | Levin et al. | |
| 2017/0354339 A1 | 12/2017 | Zeidan et al. | |
| 2017/0354364 A1 | 12/2017 | Bar-Tal et al. | |
| 2018/0008203 A1 | 1/2018 | Iyun et al. | |
| 2018/0028084 A1 | 2/2018 | Williams et al. | |
| 2018/0049803 A1 | 2/2018 | Solis | |
| 2018/0085064 A1 | 3/2018 | Auerbach et al. | |
| 2018/0132749 A1 | 5/2018 | Govari et al. | |
| 2018/0137687 A1 | 5/2018 | Katz et al. | |
| 2018/0160936 A1 | 6/2018 | Govari et al. | |
| 2018/0160978 A1 | 6/2018 | Cohen et al. | |
| 2018/0168511 A1 | 6/2018 | Hall et al. | |
| 2018/0184982 A1 | 7/2018 | Basu et al. | |
| 2018/0192958 A1 | 7/2018 | Wu | |
| 2018/0206792 A1 | 7/2018 | Auerbach et al. | |
| 2018/0235692 A1 | 8/2018 | Efimov et al. | |
| 2018/0249959 A1 | 9/2018 | Osypka | |
| 2018/0256109 A1 | 9/2018 | Wu et al. | |
| 2018/0279954 A1 | 10/2018 | Hayam et al. | |
| 2018/0303414 A1 | 10/2018 | Toth et al. | |
| 2018/0310987 A1 | 11/2018 | Altmann et al. | |
| 2018/0311497 A1 | 11/2018 | Viswanathan et al. | |
| 2018/0338722 A1 | 11/2018 | Altmann et al. | |
| 2018/0344188 A1 | 12/2018 | Govari | |
| 2018/0344202 A1 | 12/2018 | Bar-Tal et al. | |
| 2018/0344251 A1 | 12/2018 | Harlev et al. | |
| 2018/0344393 A1 | 12/2018 | Gruba et al. | |
| 2018/0360534 A1 | 12/2018 | Teplitsky et al. | |
| 2018/0365355 A1 | 12/2018 | Auerbach et al. | |
| 2019/0000540 A1 | 1/2019 | Cohen et al. | |
| 2019/0008582 A1 | 1/2019 | Govari et al. | |
| 2019/0015007 A1 | 1/2019 | Rottmann et al. | |
| 2019/0030328 A1 | 1/2019 | Stewart et al. | |

(56)  References Cited

U.S. PATENT DOCUMENTS

| | | |
|---|---|---|
| 2019/0053708 A1 | 2/2019 | Gliner |
| 2019/0059766 A1 | 2/2019 | Houben et al. |
| 2019/0069950 A1 | 3/2019 | Viswanathan et al. |
| 2019/0069954 A1 | 3/2019 | Cohen et al. |
| 2019/0117111 A1 | 4/2019 | Osadchy et al. |
| 2019/0117303 A1 | 4/2019 | Claude et al. |
| 2019/0117315 A1 | 4/2019 | Keyes et al. |
| 2019/0125439 A1 | 5/2019 | Rohl et al. |
| 2019/0133552 A1 | 5/2019 | Shemesh et al. |
| 2019/0142293 A1 | 5/2019 | Solis |
| 2019/0164633 A1 | 5/2019 | Ingel et al. |
| 2019/0167137 A1 | 6/2019 | Bar-Tal et al. |
| 2019/0167140 A1 | 6/2019 | Williams et al. |
| 2019/0188909 A1 | 6/2019 | Yellin et al. |
| 2019/0201664 A1 | 7/2019 | Govari |
| 2019/0209089 A1 | 7/2019 | Baram et al. |
| 2019/0216346 A1 | 7/2019 | Ghodrati et al. |
| 2019/0216347 A1 | 7/2019 | Ghodrati et al. |
| 2019/0231421 A1 | 8/2019 | Viswanathan et al. |
| 2019/0231423 A1 | 8/2019 | Weinkam et al. |
| 2019/0239811 A1 | 8/2019 | Just et al. |
| 2019/0246935 A1 | 8/2019 | Govari et al. |
| 2019/0298442 A1 | 10/2019 | Ogata et al. |
| 2019/0314083 A1 | 10/2019 | Herrera et al. |
| 2019/0328260 A1 | 10/2019 | Zeidan et al. |
| 2019/0343580 A1 | 11/2019 | Nguyen et al. |
| 2020/0000518 A1 | 1/2020 | Kiernan et al. |
| 2020/0008705 A1 | 1/2020 | Ziv-Ari et al. |
| 2020/0008869 A1 | 1/2020 | Byrd |
| 2020/0009378 A1 | 1/2020 | Stewart et al. |
| 2020/0015890 A1 | 1/2020 | To et al. |
| 2020/0022653 A1 | 1/2020 | Moisa |
| 2020/0029845 A1 | 1/2020 | Baram et al. |
| 2020/0046421 A1 | 2/2020 | Govari |
| 2020/0046423 A1 | 2/2020 | Viswanathan et al. |
| 2020/0060569 A1 | 2/2020 | Tegg |
| 2020/0077959 A1 | 3/2020 | Altmann et al. |
| 2020/0093539 A1 | 3/2020 | Long et al. |
| 2020/0129089 A1 | 4/2020 | Gliner et al. |
| 2020/0129125 A1 | 4/2020 | Govari et al. |
| 2020/0129128 A1 | 4/2020 | Gliner et al. |
| 2020/0179650 A1 | 6/2020 | Beeckler et al. |
| 2020/0196896 A1 | 6/2020 | Solis |
| 2020/0205689 A1 | 7/2020 | Squires et al. |
| 2020/0205690 A1 | 7/2020 | Williams et al. |
| 2020/0205737 A1 | 7/2020 | Beeckler |
| 2020/0205876 A1 | 7/2020 | Govari |
| 2020/0205892 A1 | 7/2020 | Viswanathan et al. |
| 2020/0206461 A1 | 7/2020 | Govari et al. |
| 2020/0206498 A1 | 7/2020 | Arora et al. |
| 2020/0289197 A1 | 9/2020 | Viswanathan et al. |
| 2020/0297234 A1 | 9/2020 | Houben et al. |
| 2020/0297281 A1 | 9/2020 | Basu et al. |
| 2020/0305726 A1 | 10/2020 | Salvestro et al. |
| 2020/0305946 A1 | 10/2020 | DeSimone et al. |
| 2020/0397328 A1 | 12/2020 | Altmann et al. |
| 2020/0398048 A1 | 12/2020 | Krimsky et al. |
| 2021/0015549 A1 | 1/2021 | Haghighi-Mood et al. |
| 2021/0022684 A1 | 1/2021 | Govari et al. |
| 2021/0045805 A1 | 2/2021 | Govari et al. |
| 2021/0059549 A1 | 3/2021 | Urman et al. |
| 2021/0059550 A1 | 3/2021 | Urman et al. |
| 2021/0059608 A1 | 3/2021 | Beeckler et al. |
| 2021/0059743 A1 | 3/2021 | Govari |
| 2021/0059747 A1 | 3/2021 | Krans et al. |
| 2021/0077184 A1 | 3/2021 | Basu et al. |
| 2021/0082157 A1 | 3/2021 | Rosenberg et al. |
| 2021/0085200 A1 | 3/2021 | Auerbach et al. |
| 2021/0085204 A1 | 3/2021 | Auerbach et al. |
| 2021/0085215 A1 | 3/2021 | Auerbach et al. |
| 2021/0085387 A1 | 3/2021 | Amit et al. |
| 2021/0093292 A1 | 4/2021 | Baram et al. |
| 2021/0093294 A1 | 4/2021 | Shemesh et al. |
| 2021/0093374 A1 | 4/2021 | Govari et al. |
| 2021/0093377 A1 | 4/2021 | Herrera et al. |
| 2021/0100612 A1 | 4/2021 | Baron et al. |
| 2021/0113822 A1 | 4/2021 | Beeckler et al. |
| 2021/0127999 A1 | 5/2021 | Govari et al. |
| 2021/0128010 A1 | 5/2021 | Govari et al. |
| 2021/0133516 A1 | 5/2021 | Govari et al. |
| 2021/0145282 A1 | 5/2021 | Bar-Tal et al. |
| 2021/0169421 A1 | 6/2021 | Govari |
| 2021/0169568 A1 | 6/2021 | Govari et al. |
| 2021/0177294 A1 | 6/2021 | Gliner et al. |
| 2021/0177356 A1 | 6/2021 | Gliner et al. |
| 2021/0178166 A1 | 6/2021 | Govari et al. |
| 2021/0186363 A1 | 6/2021 | Gliner et al. |
| 2021/0187241 A1 | 6/2021 | Govari et al. |
| 2021/0196372 A1 | 7/2021 | Altmann et al. |
| 2021/0196394 A1 | 7/2021 | Govari et al. |
| 2021/0212591 A1 | 7/2021 | Govari et al. |
| 2021/0219904 A1 | 7/2021 | Yarnitsky et al. |
| 2021/0278936 A1 | 9/2021 | Katz et al. |
| 2021/0282659 A1 | 9/2021 | Govari et al. |
| 2021/0307815 A1 | 10/2021 | Govari et al. |
| 2021/0308424 A1 | 10/2021 | Beeckler et al. |
| 2021/0338319 A1* | 11/2021 | Govari .............. A61B 18/1492 |
| 2023/0012307 A1* | 1/2023 | Harlev .............. A61B 18/1492 |

FOREIGN PATENT DOCUMENTS

| | | |
|---|---|---|
| EP | 0668740 A1 | 8/1995 |
| EP | 0644738 B1 | 3/2000 |
| EP | 0727183 B1 | 11/2002 |
| EP | 0727184 B1 | 12/2002 |
| EP | 2783651 A1 | 10/2014 |
| EP | 2699151 B1 | 11/2015 |
| EP | 2699152 B1 | 11/2015 |
| EP | 2699153 B1 | 12/2015 |
| EP | 2498706 B1 | 4/2016 |
| EP | 2578173 B1 | 6/2017 |
| EP | 3238645 A1 | 11/2017 |
| EP | 2884931 B1 | 1/2018 |
| EP | 2349440 B1 | 8/2019 |
| EP | 3318211 B1 | 12/2019 |
| EP | 3581135 A1 | 12/2019 |
| EP | 2736434 B1 | 2/2020 |
| EP | 3451962 B1 | 3/2020 |
| EP | 3972510 A1 | 3/2022 |
| WO | 9421167 A1 | 9/1994 |
| WO | 9421169 A1 | 9/1994 |
| WO | 9625095 A1 | 8/1996 |
| WO | 9634560 A1 | 11/1996 |
| WO | 0182814 B1 | 5/2002 |
| WO | 2004087249 A2 | 10/2004 |
| WO | 2012100185 A2 | 7/2012 |
| WO | 2013052852 A1 | 4/2013 |
| WO | 2013162884 A1 | 10/2013 |
| WO | 2013173917 A1 | 11/2013 |
| WO | 2013176881 A1 | 11/2013 |
| WO | 2014176205 A1 | 10/2014 |
| WO | 2016019760 A1 | 2/2016 |
| WO | 2016044687 A1 | 3/2016 |
| WO | 2018111600 A1 | 6/2018 |
| WO | 2018191149 A1 | 10/2018 |
| WO | 2019084442 A1 | 5/2019 |
| WO | 2019143960 A1 | 7/2019 |
| WO | 2020026217 A1 | 2/2020 |
| WO | 2020206328 A1 | 10/2020 |

* cited by examiner

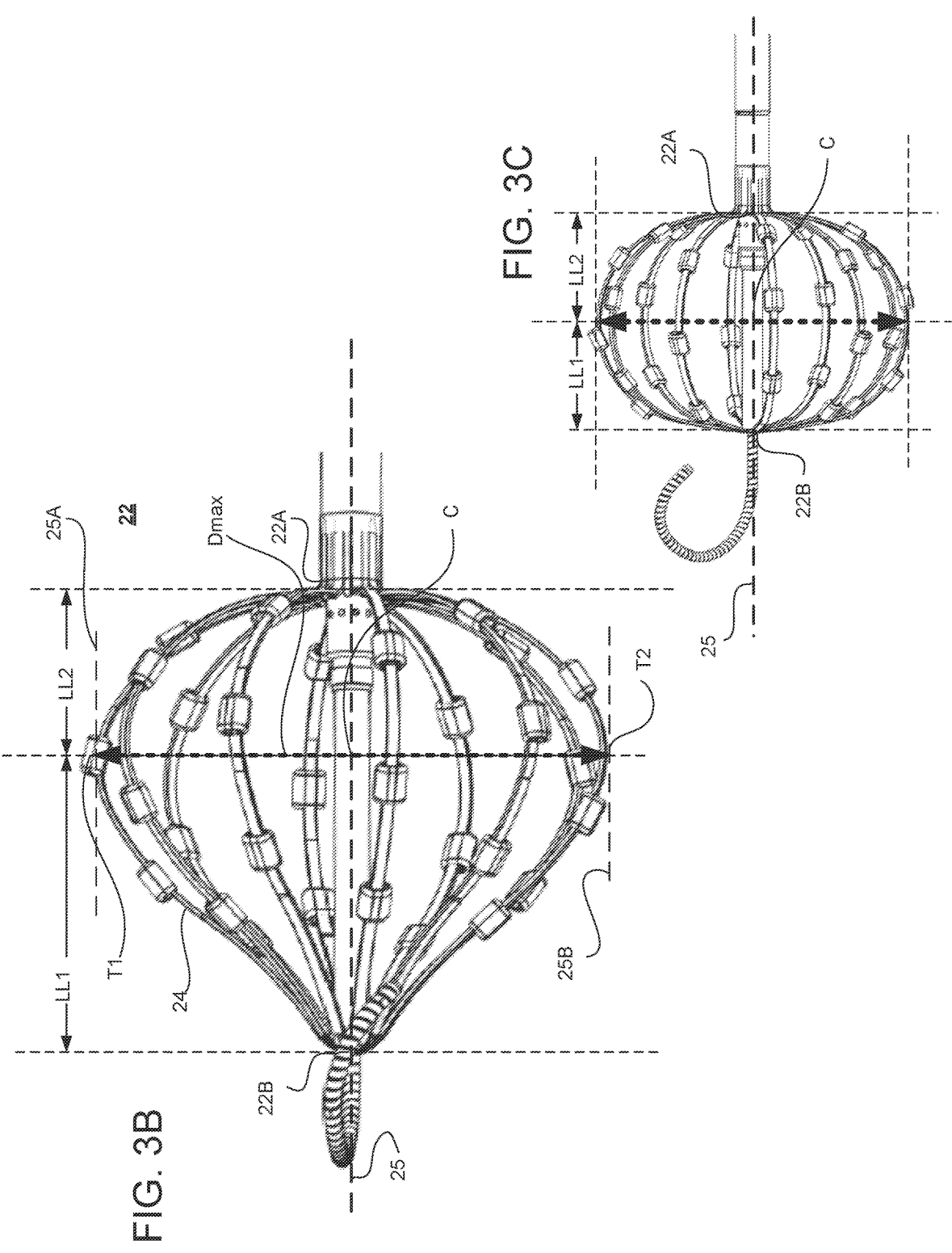

DIRECTION OF ELONGATION

MULTI-FORM CATHETER

FIELD OF THE DISCLOSURE

The present disclosure relates to medical devices, and in particular, but not exclusively to, catheter devices.

BACKGROUND

Cardiac arrhythmia, such as atrial fibrillation, occurs when regions of cardiac tissue abnormally conduct electric signals to adjacent tissue, thereby disrupting the normal cardiac cycle and causing asynchronous rhythm. Important sources of undesired signals are located in the tissue region along the pulmonary veins of the left atrium and in the superior pulmonary veins. In this condition, after unwanted signals are generated in the pulmonary veins or conducted through the pulmonary veins from other sources, they are conducted into the left atrium where they can initiate or continue arrhythmia.

Procedures for treating arrhythmia include surgically disrupting the origin of the signals causing the arrhythmia, as well as disrupting the conducting pathway for such signals. By mapping the electrical properties of the endocardium and the heart volume, and selectively ablating cardiac tissue by application of energy, it is sometimes possible to cease or modify the propagation of unwanted electrical signals from one portion of the heart to another. The ablation process destroys the unwanted electrical pathways by formation of non-conducting lesions.

In this two-step procedure, mapping followed by ablation, electrical activity at points in the heart is typically sensed and measured by advancing a catheter containing one or more electrical sensors into the heart, and acquiring data at a multiplicity of points. These data are then utilized to select the target areas at which ablation is to be performed commonly using the same catheter or a different catheter.

BRIEF DESCRIPTION OF THE DRAWINGS

The present disclosure will be understood from the following detailed description, taken in conjunction with the drawings in which:

FIG. 3B is a plan view of the teardrop catheter of FIG. 1 with certain dimensions provided;

FIG. 3C is a plan view of the catheter of FIG. 1 with the distal end of the basket being pulled proximally to force the basket to assume a spheroidal shape;

DESCRIPTION OF EXAMPLES

Overview

Figure 1:
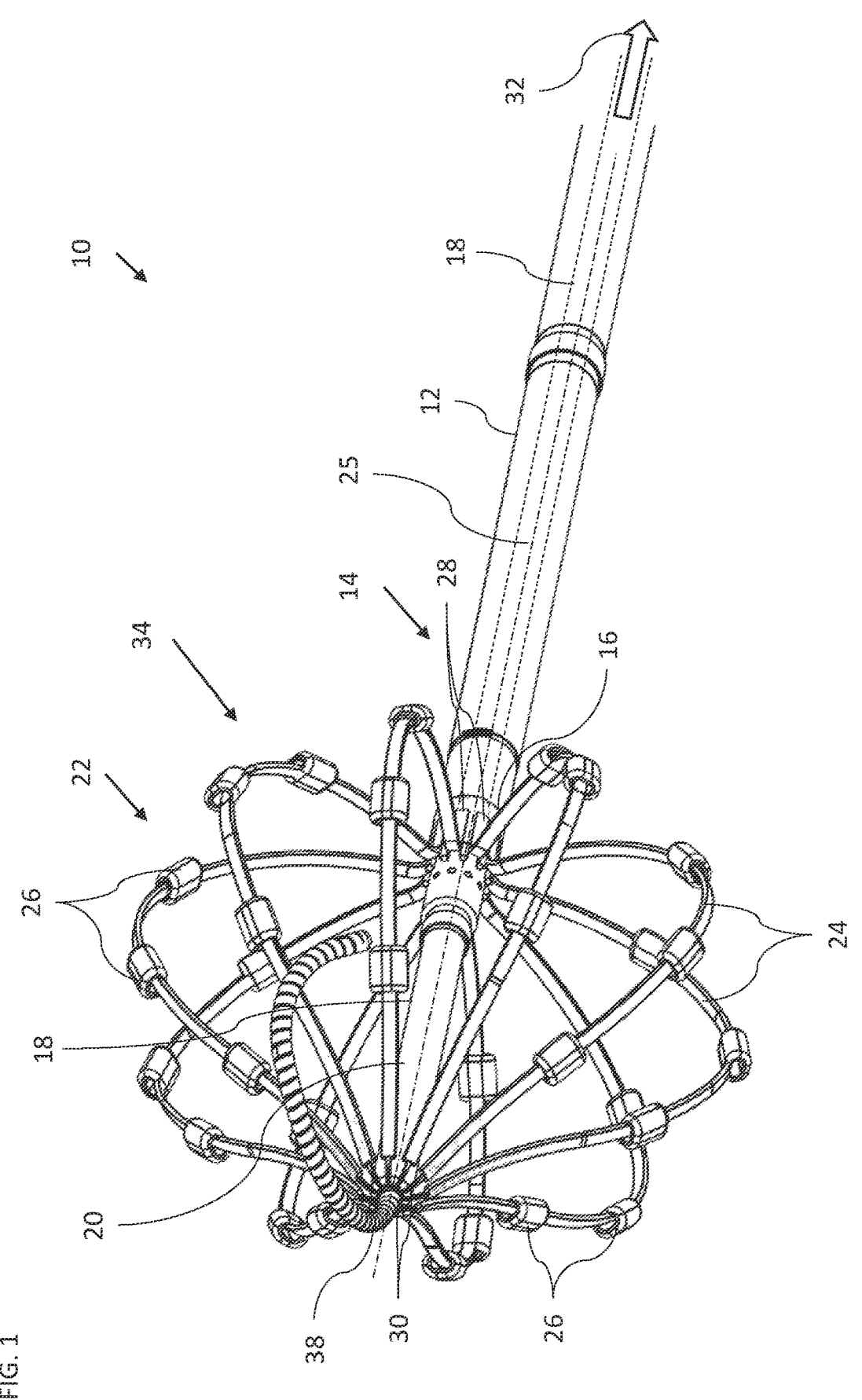
FIG. 1 is a schematic view of a catheter in a relaxed form constructed and operative in accordance with an exemplary mode of the present disclosure.

Different catheter distal end shapes may perform different tasks better than others. For example, a more conical shape catheter distal end assembly may be more useful in conical regions of the heart, such as the pulmonary vein, whereas in other regions a more spherical shaped catheter distal end assembly may provide a larger diameter for a wider circumferential ablation. One solution is to insert different catheters into the heart chamber for different tasks. However, using different catheters may complicate the procedure and result in delays which could result in medical problems.

One solution is to provide a catheter, such as a basket catheter, which can change shape to accommodate the challenges presented by some of the different tasks. A common way to change the shape of the basket is to use a tube, e.g., polymer tube, which is fed through the catheter shaft and deflectable element and is connected to the distal end of the basket. The proximal end of the basket is connected to the distal end of the deflectable element. Advancing and retracting the tube through the shaft changes the shape of the basket. However, the tube makes the basket too rigid so that if the basket is pushed against the heart tissue, the basket does not deform sufficiently with respect to the tissue and electrodes of the catheter do not sufficiently contact the tissue for mapping and/or ablation purposes. Additionally, a rigid catheter could pose a trauma risk to the patient.

Therefore, some exemplary modes of the present disclosure solve at least some of the above problems by providing a catheter including an expandable assembly having resilient splines or spines that form a basket. The resilient splines bow outward when the expandable assembly is in a relaxed form. A flexible puller extends from a proximal end of the catheter to the distal end of the expandable assembly where the puller is coupled with the distal ends of the splines. The puller may be retracted (e.g., by about 0.5 centimeters depending on the size and configuration of the expandable assembly) to cause the splines to bow further radially outward expanding the expandable assembly from the relaxed form to an expanded form. As used herein, the term "splines" or "spines" means an elongated structural member with various cross-sections and such term "splines" or "spines" may be used interchangeably.

In some disclosed modes, the relaxed form of the expandable assembly defines a pear-shaped surface. In some disclosed modes, the pear-shaped surface comprises a convex-shaped region followed by a concave-shaped region in a direction progressing away from the distal end of the deflectable element. The pear shape is suited for narrower and/or conical regions of the heart chamber, e.g., for single shot pulmonary vein isolation. The expanded form has a more spherical shape more suited to wider circumferential ablations. Retracting the puller by different amounts may result in more than two forms of the expandable assembly.

As the catheter uses a flexible puller to adjust the shape of the expandable assembly, the assembly is very flexible and can be deformed when pressed against tissue so that there is sufficient contact between electrodes of the assembly and the tissue for mapping and/or ablation (such as irreversible electroporation IRE)).

The splines flatten and transform the expandable assembly from the relaxed form to a collapsed form when the expandable assembly is pulled into a sheath, which applies a radial compressive force on the splines. The puller is optionally stretchable and stretches as the splines are flattened in the collapsed form of the assembly. In some disclosed modes, the puller includes a stretchable woven tube. For example, if the catheter is about 1 meter long, and the length of the assembly increases by 1 centimeter between the relaxed form and the compressed form, the puller needs to stretch by about 1%.

Each resilient spline may include a spring alloy element, such as a nickel titanium elongated element, a spring tempered stainless steel element, or a beryllium copper (BeCu) element. The resilient spline optionally includes a polymer tube at least partially covering the spring alloy element. One or more electrodes may then be mounted on each spline on, or around, the polymer tube.

System Description

Reference is now made to FIG. 1, which is a schematic view of a catheter 10 in a relaxed form constructed and operative in accordance with an example of the present disclosure. The catheter 10 includes an elongated deflectable element 12 including a distal end 14. The catheter 10 may include a coupler 16 connected to the distal end 14 of the elongated deflectable element 12. The catheter 10 includes a flexible puller 18 including a distal portion 20, and configured to be retracted through the deflectable element 12. The catheter 10 may include a handle or manipulator (not shown) which is configured to retract the puller 18 in the elongated deflectable element 12 in the direction shown by arrow 32.

The catheter 10 includes an expandable assembly 22 comprising a plurality of resilient splines 24 (only two labeled for the sake of simplicity). Each resilient spline 24 includes at least one electrode 26 disposed thereon. In the example of FIG. 1, the expandable assembly 22 includes ten splines 24 with three electrode 26 disposed on each spline 24. The expandable assembly 22 may include any suitable number of splines 24 (e.g., 4 or more splines 24) and any suitable number of electrodes 26 (e.g., one or more electrodes 26) per spline 24. The splines 24 and electrodes 26 are described in more detail with reference to FIG. 3A.

The resilient splines 24 are disposed circumferentially around the distal portion 20 of the puller 18 and around a longitudinal axis 25 of the catheter 10, with first ends 28 (only some labeled for the sake of simplicity) of the splines 24 being coupled with the distal end of the deflectable element (e.g., via the coupler 16) and second ends 30 (only some labeled for the sake of simplicity) of the splines 24 coupled with the distal portion of the puller 18. The ends 28 of splines 24 may be coupled to the outside of the coupler 16 or the inside of the coupler 16 using adhesive or a pressure fit, for example. The ends 30 of splines 24 may be connected together using an adhesive or via a coupler (not shown) using adhesive or a pressure fit, for example.

The splines 24 are configured to bow radially outward (from the distal portion 20 of the puller 18) in a relaxed form 34 of the expandable assembly 22. The relaxed form 34 of the expandable assembly 22 generally describes a pear-shaped surface described in more detail with reference to FIG. 3A. In some exemplary modes, the relaxed form 34 may have any suitable shape. The term "relaxed form", as used in the specification and claims, is defined as a form that the expandable assembly 22 takes when no external force (external to the expandable assembly 22) is exerted on the expandable assembly 22. If an external force is exerted on the expandable assembly 22 (for example by retracting the puller 18 in the elongated deflectable element 12, or retracting the expandable assembly 22 into a sheath, or by pressing the expandable assembly 22 against tissue of a heart chamber), the splines 24 will generally deform. Once the external force is removed, the expandable assembly 22 returns to the relaxed form 34 of the expandable assembly 22 with the splines 24 bowing radially outward from the distal portion 20 of the puller 18. The splines 24 are configured to bow further radially outward when the puller 18 is retracted (arrow 32) in the elongated deflectable element 12 expanding the expandable assembly 22 from the relaxed form 34 to an expanded form 36 shown in FIG. 2. FIG. 1 also shows the distal end of a guidewire 38. The rest of the guidewire 38 is disposed in a lumen of the puller 18 and the elongated deflectable element 12. The guidewire 38 may be used to help position the catheter 10 in a body part of a living subject.

Figure 2:
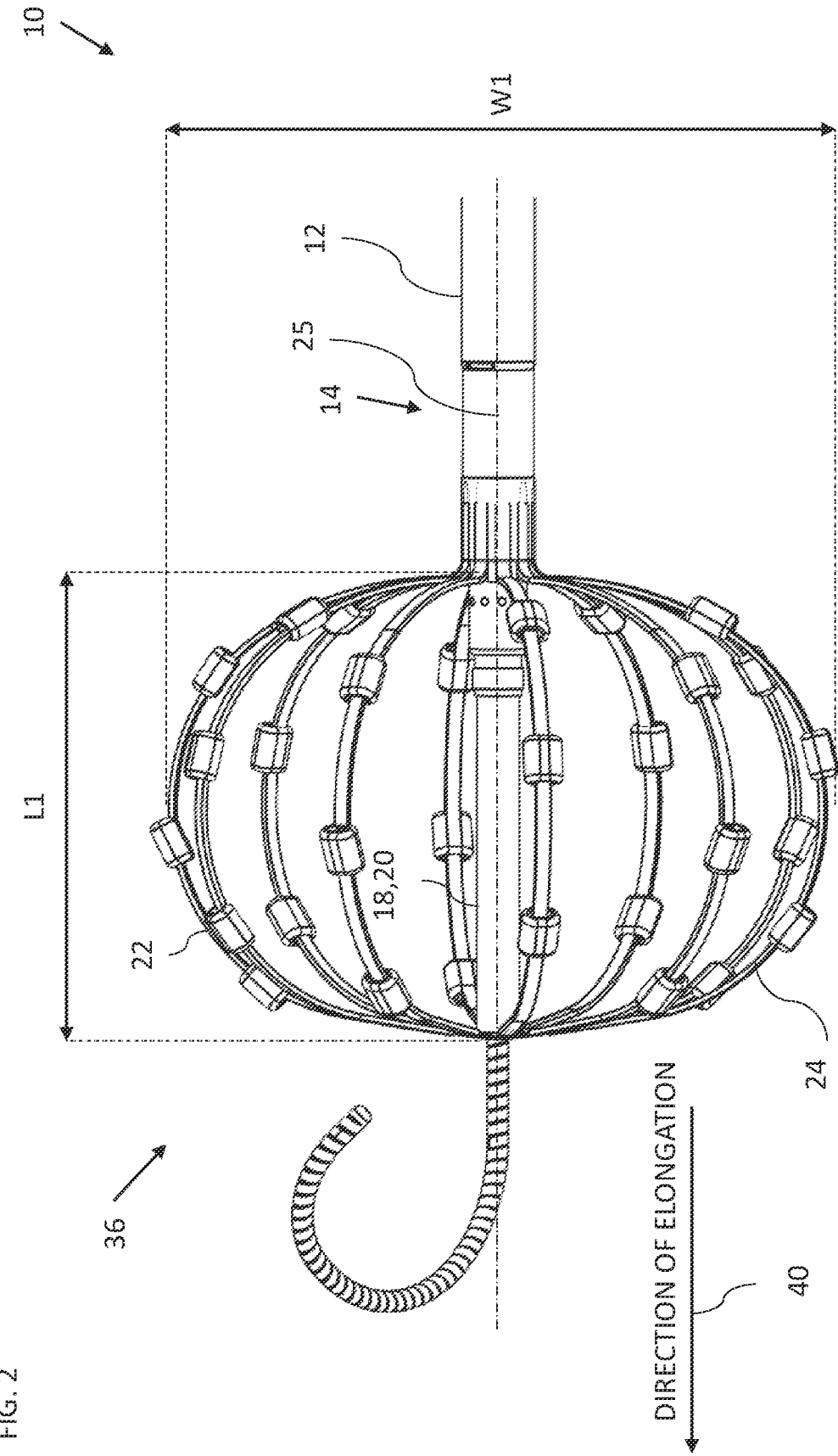
FIG. 2 is a schematic view of the catheter of FIG. 1 in an expanded form.

Reference is now made to FIG. 2, which is a schematic view of the catheter 10 of FIG. 1 in the expanded form 36 of the expandable assembly 22. As previously mentioned, the splines 24 are configured to bow further radially outward (from the distal portion 20 of the puller 18) around the longitudinal axis 25 when the puller 18 is retracted in the elongated deflectable element 12 expanding the expandable assembly 22 from the relaxed form 34 to the expanded form 36. The expanded form 36 of the expandable assembly 22 has a more spherical shape with a large width than the relaxed form 34 (FIG. 1) of the expandable assembly 22 and is more suited to wider circumferential ablations. Retracting the puller 18 by different amounts may result in more than two forms of the expandable assembly 22. In some exemplary modes, the splines 24 are configured to bow further radially outward when the puller 18 is retracted by around 0.5 centimeters expanding the expandable assembly 22 from the relaxed form 34 (FIG. 1) to the expanded form 36. The expanded form 36 of the expandable assembly 22 may have any suitable dimensions (e.g., length and width, maximum diameter). In some exemplary modes, an extent (e.g., length L1) of the expanded form 36 of the expandable assembly 22 measured in a direction parallel to a direction of elongation 40 of the distal end 14 is in a range of 30 to 35 millimeters. In some exemplary modes, a maximum width (e.g., width W1) of the expandable assembly 22 in the expanded form 36 is in a range of 28 to 33 millimeters.

Figure 3A:
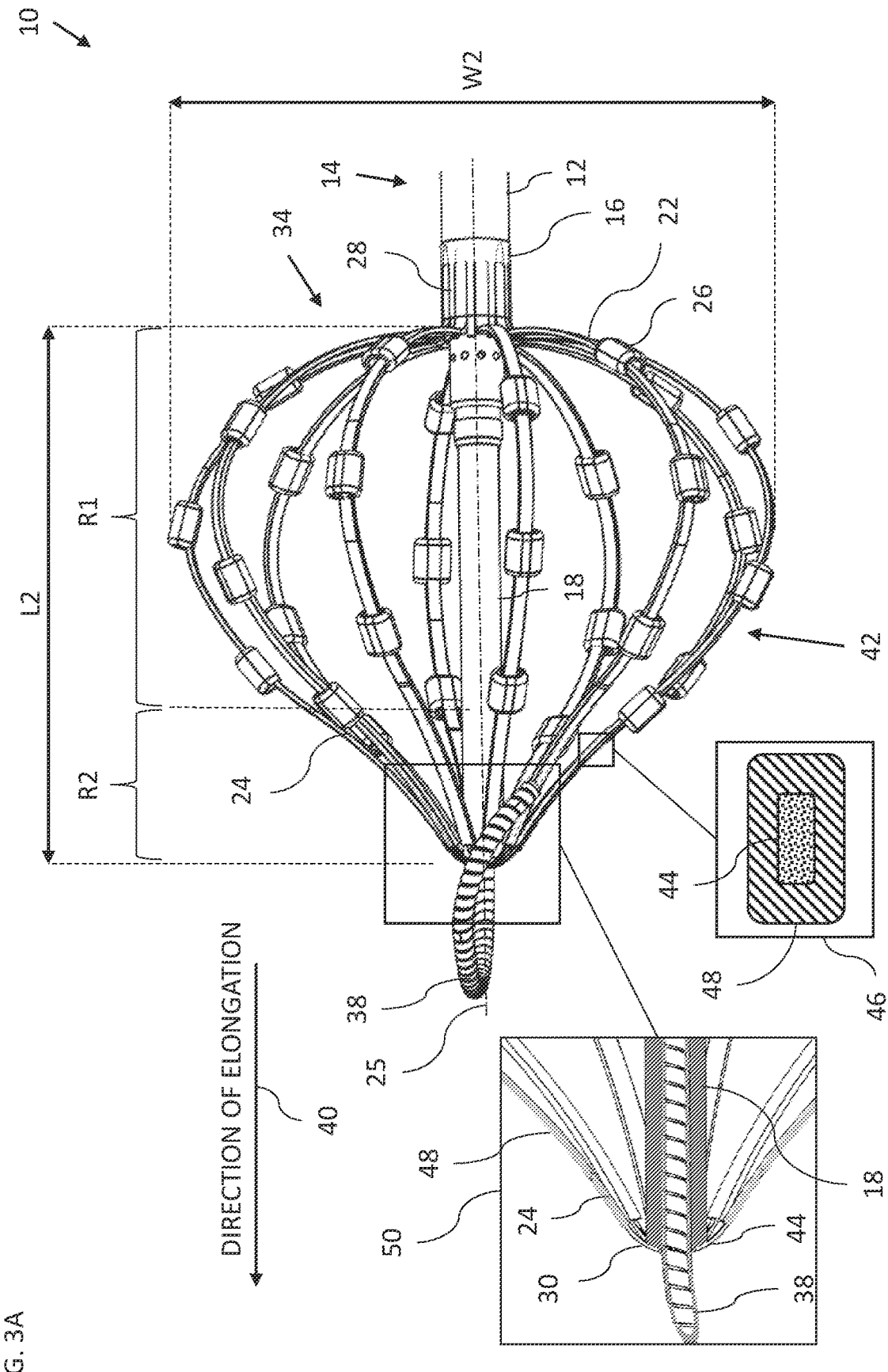
FIG. 3A is a more detail schematic view of the catheter of FIG. 1 in the relaxed form.

Reference is now made to FIG. 3A, which is a more detail schematic view of the catheter 10 of FIG. 1 in the relaxed form 34. In some exemplary modes, the relaxed form 34 of the expandable assembly 22 defines a pear-shaped surface 42 around the longitudinal axis 25. The pear-shaped surface 42 comprises a convex-shaped region R1 followed by a concave-shaped region R2 in a direction progressing away from the distal end 14 of the deflectable element 12. The relative sizes of the convex-shaped region R1 and the concave-shaped region R2 may take any suitable values. In some exemplary modes, the concave-shaped region R2 is at least 10 percent of the surface area of the pear-shaped surface 42.

Reference is now made to FIG. 3B which illustrates the basket assembly 22 of FIG. 3A with certain dimensions defined. Specifically, basket 22 has a proximal end 22A that extends along a longitudinal axis 25 to a distal end 22B. Basket 22 has a plurality of spines 24 disposed angularly about the longitudinal axis 25. Each spine 24 has a plurality of electrodes disposed thereon. Of note is the teardrop shape of the basket assembly 22 in which the diameter Dmax of the basket can be determined as where diametrically outer surface of opposed spines are tangential to a axes 25A and 25 parallel to the longitudinal axis 25, indicated here at T1 and T2. A line connecting T1 and T2 perpendicular to axis 25 at center C defines the maximum diameter of the basket assembly 22. Because of the teardrop configuration, it can be seen that a first distance LL1 from the distal end 22B of the basket 22 to the center C of Dmax is greater than the second distance LL2 from the proximal end 22A to the center of Dmax. First length LL1 may have twice the magnitude of second length LL2 in the relaxed configuration of basket 22.

When the puller 18 is pulled proximally (towards the operator) the basket assembly 22 moves from a teardrop shape to a spheroidal shape shown in FIG. 3C. In FIG. 3C, it can be seen that the first length LL1 from the distal end 22B to the center C of the maximum diameter Dmax is approximately equal to the second length LL2 from the center C to the proximal end 22A.

The splines 24 may be formed from any suitable material or materials. In some exemplary modes, each spline 24 includes a spring alloy elongated element 44 extending from the end 28 connected to the coupler 16 to the end 30 connected to the other splines 24. In some exemplary modes, the spring alloy elongated element 44 includes a nickel titanium (e.g., Nitinol®) elongated element, or a spring tempered stainless steel elongated element, or a beryllium copper (BeCu)) elongated element. The splines may have any suitable dimensions which provide the expandable assembly 22 with both suitable resilience and flexibility. In one example, the splines are about 0.004 inches thick and about 0.022 inches wide. The splines may have any suitable cross-section, e.g., square, square with rounded edges, or curved. Each spline 24 may include a polymer tube 48 (e.g., formed from polyether block amide (such as PEBAX®), polyurethane, styrene-ethylene-butylene-styrene thermoplastic elastomer (SEBS), and/or polyethylene terephthalate (PET)) at least partially covering the spring alloy (e.g., nickel titanium) elongated element 44. A cross-section of one of the splines 24 is shown in inset 46. An inset 50 shows a cross-sectional view of the distal end of the expandable assembly 22. The inset 50 shows the spring alloy elongated elements 44 of the splines 24 being connected to the puller 18. The inset 50 also shows the guidewire 38 in the lumen of the puller 18.

In some exemplary modes, the electrode(s) 26 are mounted over the polymer tube 48. A respective wire (not shown) is connected to the inner surface of each respective electrode 26. The respective wire is fed through a respective hole (not shown) in the polymer tube 48 and through the lumen of the polymer tube 48 to the coupler 16 or the elongated deflectable element 12. The wires from the different electrodes 26 may then run through the elongated deflectable element 12 to a proximal end of the catheter 10. The electrodes 26 may be formed from any suitable material, for example, gold or stainless steel, and have any suitable shaped. In some exemplary modes, the electrode 26 are biased to have more bulk facing outside the expandable assembly 22.

The relaxed form 34 of the expandable assembly 22 may have any suitable dimensions (e.g., length and width, maximum diameter). In some exemplary modes, an extent (e.g., length L2) of the relaxed form 34 of the expandable assembly 22 measured in a direction parallel to the direction of elongation 40 of the distal end 14 is in a range of 35 to 45 millimeters. In some exemplary modes, a maximum width (e.g., W2) of the expandable assembly 22 in the relaxed form 34 is in a range of 25 to 30 millimeters.

Figures 4, 5:
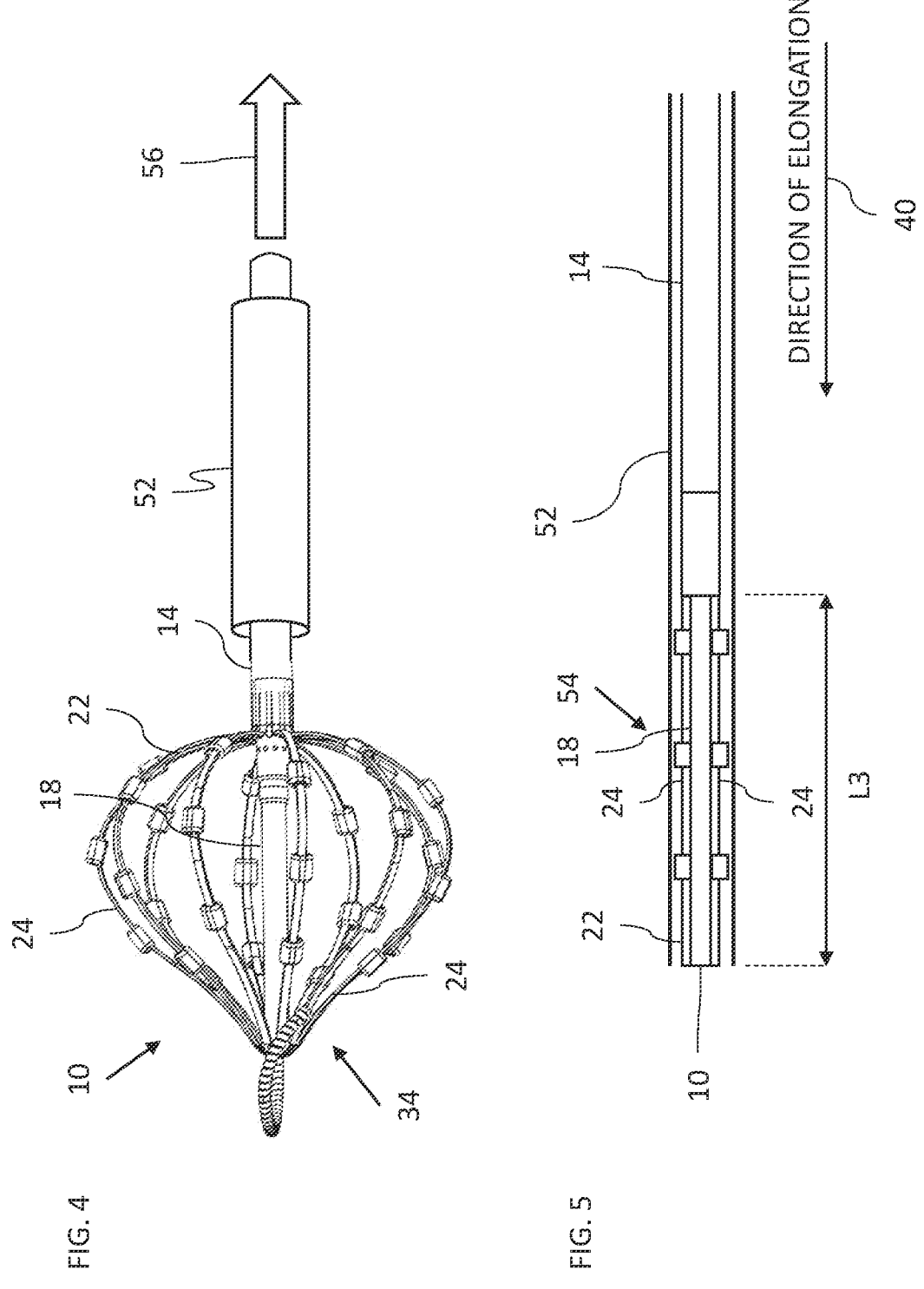
FIG. 4 is a schematic view of the catheter of FIG. 1 being retracted into a sheath.
FIG. 5 is a schematic cross-sectional view of the catheter of FIG. 1 in the sheath of FIG. 4.

Reference is now made to FIGS. 4 and 5. FIG. 4 is a schematic view of the catheter 10 of FIG. 1 being retracted into a sheath 52. FIG. 5 is a schematic cross-sectional view of the catheter 10 of FIG. 1 retracted into the sheath 52 of FIG. 4. The splines 24 are configured to flatten and transform the relaxed form 34 of the expandable assembly 22 to a collapsed form 54 of the expandable assembly 22 when the expandable assembly 22 is pulled (arrow 56) into the sheath 52, which applies a radial compressive force on the splines 24. In some exemplary modes, an extent (e.g., length L3) of the collapsed form 54 measured in a direction parallel to the direction of elongation 40 of the distal end 14 is in a range of 35 to 45 millimeters.

In some exemplary modes, the puller 18 is stretchable and is configured to stretch as the splines 24 are flattened. In some disclosed modes, the puller 18 includes a stretchable woven tube. The stretchable woven tube may be formed from a braided polymer tube, including for example, a substrate of PEBAX with an LCP filament or yarn used for braiding and then PEBAX film cast over the braiding. Suitable polymer tubes are commercially available from Putnam Plastics Corporation Dayville, CT 06241, United States, and MicroLumen high performance medical tubing, Oldsmar, FL 34677 USA.

In some disclosed modes, the puller 18 may be a stretchable wire. In some exemplary modes, the puller 18 is stretchable by about 1 percent. For example, if the catheter 10 is about 1 meter long and the length of the assembly increases by 1 centimeter between the relaxed form 34 and the compressed form 54, the puller 18 needs to stretch by about 1%. In some exemplary modes, the puller is stretchable by at least 0.5 percent.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 72% to 108%.

EXAMPLES

Example 1: A catheter apparatus (10), comprising: an elongated deflectable element (12) including a distal end (14); a flexible puller (18) including a distal portion (20), and configured to be retracted through the deflectable element; and an expandable assembly (22) comprising a plurality of resilient splines (24), each resilient spline including at least one electrode (26) disposed thereon, the resilient splines being disposed circumferentially around the distal portion of the puller, with first ends (28) of the splines being coupled with the distal end of the deflectable element and second ends (30) of the splines coupled with the distal portion of the puller, the splines being configured to: bow radially outward in a relaxed form of the expandable assembly: and bow further radially outward when the puller is retracted expanding the expandable assembly from the relaxed form (34) to an expanded form (36).

Example 2: The apparatus according to example 1, wherein an extent (L1) of the expanded form measured in a direction parallel to a direction of elongation (40) of the distal end is in a range of 30 to 35 millimeters.

Example 3: The apparatus according to example 1 or 2, wherein an extent (L2) of the relaxed form measured in the direction parallel to the direction of elongation of the distal end is in a range of 35 to 45 millimeters.

Example 4: The apparatus according to any of examples 1-3, wherein a maximum width (W1) of the assembly in the expanded form is in a range of 28 to 33 millimeters.

Example 5: The apparatus according to any of examples 1-4, wherein a maximum width (W2) of the assembly in the relaxed form is in a range of 25 to 30 millimeters.

Example 6: The apparatus according to any of examples 1-5, wherein the splines are configured to flatten and transform the relaxed form to a collapsed form (54) of the expandable assembly when the expandable assembly is pulled into a sheath (52), which applies a radial compressive force on the splines.

Example 7: The apparatus according to example 6, wherein an extent (L3) of the collapsed form measured in a direction parallel to a direction of elongation of the distal end is in a range of 35 to 45 millimeters.

Example 8: The apparatus according to example 6 or 7, wherein the puller is stretchable and is configured to stretch as the splines are flattened.

Example 9: The apparatus according to any of examples 1-8, wherein the puller is stretchable by at least 0.5 percent.

Example 10: The apparatus according to any of examples 1-8, wherein the puller is stretchable by about 1 percent.

Example 11: The apparatus according to any of examples 1-8, wherein the puller includes a stretchable woven tube.

Example 12: The apparatus according to any of examples 1-11, wherein the relaxed form of the expandable assembly defines a pear shape surface (42).

Example 13: The apparatus according to example 12, wherein the pear-shaped surface comprises a convex-shaped region (R1) followed by a concave-shaped region (R2) in a direction progressing away from the distal end of the deflectable element.

Example 14: The apparatus according to example 13, wherein the concave-shaped region is at least 10 percent of the surface area of the pear-shaped surface.

Example 15: The apparatus according to any of examples 1-14, wherein each resilient spline includes a nickel titanium elongated element (44).

Example 16: The apparatus according to example 15, wherein each resilient spline includes a polymer tube (48) at least partially covering the nickel titanium elongated element.

Example 17: The apparatus according to any of examples 1-16, wherein the splines are configured to bow further radially outward when the puller is retracted by around 0.5 centimeters expanding the expandable assembly from the relaxed form to the expanded form.

Example 18: A basket catheter that includes a plurality of spines disposed radially around a longitudinal axis to define a basket assembly extending from a proximal end to a distal end along the longitudinal axis, the basket assembly defining a teardrop shape having a maximum diameter as measured orthogonally to a center disposed on the longitudinal axis, the basket assembly having a first length from the distal end to the center of the maximum diameter of the basket assembly and a second length as measured from the center of the maximum diameter along the longitudinal axis to the proximal end of the basket assembly, the first length being greater than the second length.

Example 19: The basket catheter of example 18 in which the first length is approximately twice the second length.

Example 20: The basket catheter of example 19 in which a plurality of electrodes is disposed on each spine.

Various features of the disclosure which are, for clarity, described in the contexts of separate examples may also be provided in combination in a single example. Conversely, various features of the disclosure which are, for brevity, described in the context of a single example may also be provided separately or in any suitable sub-combination.

The examples described above are cited by way of example, and the present disclosure is not limited by what has been particularly shown and described hereinabove. Rather the scope of the disclosure includes both combinations and sub-combinations of the various features described hereinabove, as well as variations and modifications thereof which would occur to persons skilled in the art upon reading the foregoing description and which are not disclosed in the prior art.

What is claimed is:

1. A catheter apparatus, comprising:
an elongated deflectable element including a distal end;
a flexible puller including a distal portion, and configured to be retracted through the deflectable element; and
an expandable assembly comprising a plurality of resilient splines, each resilient spline including at least one electrode disposed thereon such that an outer surface of the at least one electrode is provided on the outside of the expandable assembly and an inner surface of the at least one electrode is provided on an inside of the expandable assembly, the at least one electrode being biased to have more bulk facing outside the expandable assembly, the resilient splines being disposed circumferentially around the distal portion of the puller, with first ends of the splines being coupled with the distal end of the deflectable element and second ends of the splines coupled with the distal portion of the puller, the splines being configured to:
bow radially outward in a relaxed form of the expandable assembly defining a pear-shaped surface configured for mapping or ablation, and
bow further radially outward when the puller is retracted proximally from the relaxed form, thereby expanding the expandable assembly from the relaxed form to an expanded form defining a spheroidal-shaped surface extending from the first ends of the splines to the second ends of the splines and configured for mapping or ablation.

2. The apparatus according to claim 1, wherein an extent of the expanded form measured in a direction parallel to a direction of elongation of the distal end is in a range of 30 to 35 millimeters.

3. The apparatus according to claim 1, wherein an extent of the relaxed form measured in a direction parallel to a direction of elongation of the distal end is in a range of 35 to 45 millimeters.

4. The apparatus according to claim 1, wherein a maximum width of the assembly in the expanded form is in a range of 28 to 33 millimeters.

5. The apparatus according to claim 1, wherein a maximum width of the assembly in the relaxed form is in a range of 25 to 30 millimeters.

6. The apparatus according to claim 1, wherein the splines are configured to flatten and transform the relaxed form to a collapsed form of the expandable assembly when the expandable assembly is pulled into a sheath, which applies a radial compressive force on the splines.

7. The apparatus according to claim 6, wherein an extent of the collapsed form measured in a direction parallel to a direction of elongation of the distal end is in a range of 35 to 45 millimeters.

8. The apparatus according to claim 6, wherein the puller is stretchable and is configured to stretch as the splines are flattened.

9. The apparatus according to claim 8, wherein the puller is stretchable by at least 0.5 percent.

10. The apparatus according to claim 8, wherein the puller is stretchable by about 1 percent.

11. The apparatus according to claim 8, wherein the puller includes a stretchable woven tube.

12. The apparatus according to claim 1, wherein the pear-shaped surface comprises a convex-shaped region followed by a concave-shaped region in a direction progressing away from the distal end of the deflectable element.

13. The apparatus according to claim 12, wherein the concave-shaped region is at least 10 percent of the surface area of the pear-shaped surface.

14. The apparatus according to claim 1, wherein each resilient spline includes a nickel titanium elongated element.

15. The apparatus according to claim 14, wherein each resilient spline includes a polymer tube at least partially covering the nickel titanium elongated element.

16. The apparatus according to claim 1, wherein the splines are configured to bow further radially outward when the puller is retracted by around 0.5 centimeters expanding the expandable assembly from the relaxed form to the expanded form.

17. The apparatus according to claim 1, wherein a first distance from a distal end of the expandable assembly to a maximum diameter of the expandable assembly in the relaxed form is greater than a second distance from a proximal end of the expandable assembly to the maximum diameter in the relaxed form, and wherein the first distance is approximately equal to the second distance in the expanded form.

\* \* \* \* \*